US005688662A

United States Patent [19]

Margolskee

[11] Patent Number: 5,688,662

[45] Date of Patent: Nov. 18, 1997

[54] GUSTDUCIN POLYNUCLEOTIDES, VECTORS, HOST CELLS AND RECOMBINANT METHODS

[75] Inventor: Robert F. Margolskee, Upper Montclair, N.J.

[73] Assignee: Linguagen Corporation, Basking Ridge, N.J.

[21] Appl. No.: 868,353

[22] Filed: Apr. 9, 1992

[51] Int. Cl.[6] .......................... C12P 21/06; C12N 15/00; C07H 17/00; C07K 14/435

[52] U.S. Cl. .................. 435/69.1; 435/320.1; 435/240.1; 536/231; 530/350

[58] Field of Search ........................... 530/350; 435/69.1, 435/320.1; 536/27

[56] References Cited

PUBLICATIONS

McLaughlin et al. 1992 Chem Senses 17(5):667.
Akabas et al., *Science*, 242, 1047–1050 (1988).
Avenet et al., *Nature*, 331, 351–354 (1988).
Avenet et al., *J. Membrane Biol.*, 112, 1–8 (1989).
Beidler, in Wolstenholme et al., Eds. *Ciba Found. Symp.: Taste and Smell in Vertebrates*, 51–67, Churchill, London (1970).
Birnbaumer, *Ann. Rev. Pharmacol. Toxicol.*, 30, 675–705 (1990).
Bruch et al., *J. Biol. Chem.*, 262, 2401–2404 (1987).
Cheung et al., *FEBS Letters*, 279, 277–280 (1991).
Devereaux et al., *Nucl. Acids Res.*, 12, 387–395 (1984).
Gillespie, in Beavo et al., Eds., *Cyclic Nucleotide Phosphodiesterases: Structure, Regulation and Drug Action*, Ch. 7, John Wiley and Sons Ltd., New York (1990).
Hamm et al., *Science*, 241, 832–835 (1988).
Heck et al., *Science*, 223, 403–405 (1984).
Hellekant et al., in Cagan, Ed., *Neural Mechanisms in Taste*, Ch. 4, CRC Press, Inc., Boca Raton, Florida (1989).
Higginbotham et al., in *The Quality of Foods and Beverages*, 91–111, Academic Press, Inc. (1981).
Houghten et al., *Nature*, 354, 84–86 (1991).
Jones et al., *Science*, 244, 790–795 (1989).
Kinnamon, *TINS*, 11, 491–496 (1988).
Kinnamon et al., *Proc. Natl. Acad. Sci. USA*, 85, 7023–7027 (1988).
Kinnamon et al., *J. Gen. Physiol.*, 91, 351–371 (1988).
König et al., *Proc. Natl. Acad. Sci. USA*, 86, 6878–6882 (1989).
Krieg et al., *Methods Enz.*, 155, 397–415 (1987).
Kurihara et al., *Biochem. Biophys. Res. Comm.*, 48, 30–34 (1972).
Lam et al., *Nature*, 354, 82–84 (1991).
Lerea et al., *Science*, 234, 77–80 (1986).
Lochrie et al., *Science*, 228, 96–99 (1985).
Nishizuka et al., Eds., *The Biology and Medicine of Signal Transduction*, 76–82, Raven Press, New York (1990).
Price, *Nature*, 241, 54–55 (1973).
Roper, *Ann. Rev. Neurosci.*, 12, 329–353 (1989).
Schiffman et al., *Proc. Natl. Acad. Sci. USA*, 80, 6136–6140 (1983).
Scott et al., *Science*, 249, 386–390 (1990).
Simon et al., *Science*, 252, 802–808 (1991).
Spielman et al., *Chem. Senses*, 14, 841–846 (1989).
Strathmann et al., *Proc. Natl. Acad. Sci. USA*, 86, 7407–7409 (1989).
Striem et al., *Biochem J.*, 260, 121–126 (1989).
Stryer et al., *Ann. Rev. Cell Biol.*, 2, 391–419 (1986).
Tanabe et al., *Nature*, 315, 242–245 (1985).
Tonasaki et al., *Nature*, 331, 354–356 (1988).
Sambook Molecular Cloning—A Lab Manual. Ch. 16, Cold Spr. Harbor Lab. Press, CSH, NY 1988.

*Primary Examiner*—Vasu S. Jagannathan
*Assistant Examiner*—K. Cochrane Carlson
*Attorney, Agent, or Firm*—Marshall, O'Toole, Gerstein, Murray & Borun

[57] ABSTRACT

A novel taste cell specific guanine nucleotide binding protein, gustducin, is disclosed as well as polynucleotide sequences encoding the α subunit of gustducin. Also disclosed are methods of modifying taste involving agents that inhibit or activate the gustducin α subunit, methods for identifying such taste modifying agents and various taste modifying agents.

5 Claims, 5 Drawing Sheets

```
1    GACTGGTGCCTGCTGTTGGGAGCACTGCTCTGACGATCTATCTCTAAACCACTGCTGTGCTCTG

65   TGTTTGAAAACTTTGAGCAAATCAACTGCCCGTCCTCTAACAGCAAAAGATGGGAAGTGGAATT
                                                      M  G  S  G  I

129  AGTTCAGAGAGCAAGGAGTCAGCCAAAAGGTCCAAAGAACTGGAGAAGAAGCTTCAGGAAGATG
     S  S  E  S  K  E  S  A  K  R  S  K  E  L  E  K  K  L  Q  E  D  A

193  CTGAACGAGATGCAAGAACTGTGAAGTTGCTGCTATTAGGAGCAGGTGAATCTGGAAAAAGTAC
       E  R  D  A  R  T  V  K  L  L  L  L  G  A  G  E  S  G  K  S  T

257  TATTGTTAAACAAATGAAGATCATCCACAAGAATGGTTACAGTAAACAAGAATGCATGGAGTTT
      I  V  K  Q  M  K  I  I  H  K  N  G  Y  S  K  Q  E  C  M  E  F

321  AAAGCAGTGGTTTACAGTAACACGTTGCAGTCCATCCTGGCCATTGTGAAAGCCATGACTACAC
     K  A  V  V  Y  S  N  T  L  Q  S  I  L  A  I  V  K  A  M  T  T  L

385  TAGGGATTGATTATGTCAATCCGAGAAGTAGAGAGGACCAACAACTGCTTCTCTCCATGGCAAA
       G  I  D  Y  V  N  P  R  S  R  E  D  Q  Q  L  L  L  S  M  A  N

449  CACACTAGAAGATGGTGACATGACGCCTCAGTTGGCTGAAATAATTAAACGTCTGTGGGGCGAT
      T  L  E  D  G  D  M  T  P  Q  L  A  E  I  I  K  R  L  W  G  D
```

FIGURE 1A

```
513  CCAGGAATTCAAGCCTGCTTCGAAAGGGCATCTGAATACCAGCTCAATGACTCTGCAGCTTACT
     P  G  I  Q  A  C  F  E  R  A  S  E  Y  Q  L  N  D  S  A  A  Y  Y

577  ACCTTAATGACTTAGATAGACTCACAGCCCCTGGGTATGTGCCAAATGAACAAGACGTTCTACA
       L  N  D  L  D  R  L  T  A  P  G  Y  V  P  N  E  Q  D  V  L  H

641  TTCCCGGGTGAAAACCACTGGTATCATTGAAACTCAATTCTCCTTTAAAGACTTGAACTTCAGA
      S  R  V  K  T  T  G  I  I  E  T  Q  F  S  F  K  D  L  N  F  R

705  ATGTTTGATGTAGGTGGCCAGAGATCAGAAAGAAAGAAATGGATCCACTGCTTTGAAGGAGTGA
     M  F  D  V  G  G  Q  R  S  E  R  K  K  W  I  H  C  F  E  G  V  T

769  CGTGCATTATATTTTGTGCAGCCCTAAGTGCCTACGACATGGTACTTGTAGAAGATGAAGAGGT
       C  I  I  F  C  A  A  L  S  A  Y  D  M  V  L  V  E  D  E  E  V

833  GAACAGAATGCATGAAAGTCTTCACCTCTTCAACAGCATCTGTAATCACAAGTATTTTGCAACC
      N  R  M  H  E  S  L  H  L  F  N  S  I  C  N  H  K  Y  F  A  T

897  ACCTCCATTGTTCTGTTTCTTAACAAGAAAGATCTCTTCCAGGAGAAAGTGACCAAGGTGCACC
     T  S  I  V  L  F  L  N  K  K  D  L  F  Q  E  K  V  T  K  V  H  L

961  TCAGCATCTGTTTCCCAGAATACACTGGACCAAATACATTCGAAGATGCAGGGAACTACATCAA
       S  I  C  F  P  E  Y  T  G  P  N  T  F  E  D  A  G  N  Y  I  K
```

FIGURE 1B

```
1025  GAACCAGTTCCTAGACCTGAACTTAAAAAAAGAAGATAAGGAAATCTATTCTCACATGACCTGC
       N  Q  F  L  D  L  N  L  K  K  E  D  K  E  I  Y  S  H  M  T  C

1089  GCTACTGACACACAAAACGTCAAATTCGTGTTTGATGCCGTGACAGATATAATAATAAAAGAGA
      A  T  D  T  Q  N  V  K  F  V  F  D  A  V  T  D  I  I  I  K  E  N

1153  ACCTCAAAGACTGTGGGCTCTTCTGAGCAACCTGTTTGCTACCACTTGTGATGGCTATAGTCTT
        L  K  D  C  G  L  F  *

1217  TTTAAGACATAAAAAGGTGCTGTGTATTAGCTTGGATAGATATTAACTGATTTAGAAATGTGAC

1281  TAGCATTATAAAACAAAAAAATTCACACAAAAATATTACTGTGATATCACGTATATCTGGGTAC

1345  GGTTTTCTTGGGGAATGGAGGGTAGAGTTGCTGATGTTCTAAATCTGAAATCTGATGTATCTGG

1409  TAACTGTCACAATATACATTCATGCTACTAAAGTTTTTTGGAAGTGAGCTGTAAGTGACCAATT

1473  TTTAATCATAGAGTAAACCTCAGAATGTGCTATAACATTGCCCCAGCTAGATTTTGAAAGCATT

1537  CAAAGTCATGTCTGTACTACAGAAACTGTACAAAATGAACAAGGTATAATTTTGGTCATCAGCC

1601  TTTCAATTAGGCTGCCACAAGCACACACAGTACATGCTTTTATTGATGGGAAATTGTATGTGTA

1665  AAATAAATATATATATAATAAAAAAAAAAAAAAAAAAA
```

FIGURE 1C

```
                     1                                                    50
CONSENSUS            MGsGaSaE.K e.akrSkELE KKLqEDAekd ArTVKLLLLG AGESGKSTIV
GUSTDUCIN            MGSGISSESK ESAKRSKELE KKLQEDAERD ARTVKLLLLG AGESGKSTIV
TRANSDUCIN(CONE)     MGSGASAEDK ELAKRSKELE KKLQEDADKE AKTVKLLLLG AGESGKSTIV
TRANSDUCIN(ROD)      MGAGASAEEK ....HSRELE KKLKEDAEKD ARTVKLLLLG AGESGKSTIV

                     51                                                  100
CONSENSUS            KQMKIIHqdG YS.eECLEfk AiiYgNtLQS ILAIvrAMtT LgIdY.....
GUSTDUCIN            KQMKIIHKNG YSKQECMEFK AVVYSNTLQS ILAIVKAMTT LGIDYVNPRS
TRANSDUCIN(CONE)     KQMKIIHQDG YSPEECLEYK AIIYGNVLQS ILAIIRAMPT LGIDYAEVSC
TRANSDUCIN(ROD)      KQMKIIHQDG YSLEECLEFI AIIYGNTLQS ILAIVRAMTT LNIQYGDSAR

                     101                                                 150
CONSENSUS            .dd.r.l..m AdtiEeGtMp pel.eiI.rL WkD.GiQACF dRAsEYQLND
GUSTDUCIN            REDQQLLLSM ANTLEDGDMT PQLAEIIKRL WGDPGIQACF ERASEYQLND
TRANSDUCIN(CONE)     VDNGRQLNNL ADSIEEGTMP PELVEVIRKL WKDGGVQACF DRAAEYQLND
TRANSDUCIN(ROD)      QDDARKLMHM ADTIEEGTMP KEMSDIIQRL WKDSGIQACF DRASEYQLND

                     151                                                 200
CONSENSUS            SA.YYLndLd RitaPgYvPn EQDVLrSRVK TTGIIETqFS fKDLNFRMFD
GUSTDUCIN            SAAYYLNDLD RLTAPGYVPN EQDVLHSRVK TTGIIETQFS FKDLNFRMFD
TRANSDUCIN(CONE)     SASYYLNQLD RITAPDYLPN EQDVLRSRVK TTGIIETKFS VKDLNFRMFD
TRANSDUCIN(ROD)      SAGYYLSDLE RLVTPGYVPT EQDVLRSRVK TTGIIETQFS FKDLNFRMFD
```

FIGURE 2A

```
                    201                                                    250
CONSENSUS              VGGQRSERKK WIHCFEGVTC IIFcAALSAY DMVLVEDdEV NRMHESLHLF
GUSTDUCIN              VGGQRSERKK WIHCFEGVTC IIFCAALSAY DMVLVEDEEV NRMHESLHLF
TRANSDUCIN(CONE)       VGGQRSERKK WIHCFEGVTC IIFCAALSAY DMVLVEDDEV NRMHESLHLF
TRANSDUCIN(ROD)        VGGQRSERKK WIHCFEGVTC IIFIAALSAY DMVLVEDDEV NRMHESLHLF

                    251                                                    300
CONSENSUS              NSICNHkyFA tTSIVLFLNK KDlF.EKikK vHLSICFPeY .GpNtyEDAG
GUSTDUCIN              NSICNHKYFA TTSIVLFLNK KDLFQEKVTK VHLSICFPEY TGPNTFEDAG
TRANSDUCIN(CONE)       NSICNHKFFA ATSIVLFLNK KDLFEEKIKK VHLSICFPEY DGNNSYEDAG
TRANSDUCIN(ROD)        NSICNHRYFA TTSIVLFLNK KDVFSEKIKK AHLSICFPDY NGPNTYEDAG

                    301                                                    350
CONSENSUS              NYIK.QFLdL NmrkdvKEIY SHMTCATDTQ NVKFVFDAVT DIIIKENLKD
GUSTDUCIN              NYIKNQFLDL NLKKEDKEIY SHMTCATDTQ NVKFVFDAVT DIIIKENLKD
TRANSDUCIN(CONE)       NYIKSQFLDL NMRKVDKEIY SHMTCATDTQ NVKFVFDAVT DIIIKENLKD
TRANSDUCIN(ROD)        NYIKVQFLEL NMRRDVKEIY SHMTCATDTQ NVKFVFDAVT DIIIKENLKD

                    351
CONSENSUS              CGLF
GUSTDUCIN              CGLF
TRANSDUCIN(CONE)       CGLF
TRANSDUCIN(ROD)        CGLF
```

FIGURE 2B

GUSTDUCIN POLYNUCLEOTIDES, VECTORS, HOST CELLS AND RECOMBINANT METHODS

BACKGROUND

The present invention relates, in general, to materials and methods relevant to taste transduction. More particularly, the invention relates to a heretofore unknown taste cell specific guanine nucleotide binding protein, gustducin, and to polynucleotide sequences encoding the α subunit of gustducin. The invention also relates to methods of modifying taste that involve agents which inhibit or activate the gustducin α subunit, to methods for identifying such taste modifying agents and to the taste modifying agents.

Vertebrate taste transduction is mediated by specialized neuroepithelial cells, referred to as taste receptor cells, organized into groups of forty to one hundred cells which form taste buds. Taste buds are ovoid structures, the vast majority of which are embedded within the epithelium of the tongue. Taste transduction is initiated at the apical portion of a taste bud at the taste pore where microvilli of the taste receptor cells make contact with the outside environment. Various taste stimulants (tastants) cause either depolarization (i.e., a reduction in membrane potential) or hyperpolarization (i.e., an increase in membrane potential) of taste cells and regulate neurotransmitter release from the cells at chemical synapses with afferent nerve fibers. The primary gustatory sensory fibers which receive the chemical signals enter the base of each taste bud. Lateral connections between taste cells in the same bud may also modulate the signals transmitted to the afferent nerve fibers.

There are four basic taste modalities typified by four distinct groups of taste stimuli: salty, sour, sweet, and bitter. Different taste modalities appear to function by different mechanisms. For example, salty taste appears to be mediated by sodium ion flux through apical sodium channels [see Heck et al. *Science,* 223, 403–405 (1984) and Schiffman et al., *Proc. Natl. Acad. Sci USA,* 80, 6136–6140 (1983)] and sour taste seems to be mediated via hydrogen ion blockade of potassium or sodium channels [see Kinnamon et al., *J. Gen. Physiol.,* 91, 351–371 (1988) and Kinnamon et al., *Proc. Natl. Acad. Sci. USA,* 85, 7023–7027 (1988)].

Of particular interest to the background of the present invention are guanine nucleotide binding proteins (G proteins) which have been specifically implicated in the transduction of sweet and bitter tastes and may also be involved in the regulation of the ion channels involved in transduction of salty and sour tastes. See, for example, the recent reviews on G proteins: Birnbaumer, *Ann. Rev. Pharmacol. Toxicol.,* 30, 675–705 (1990) and Simon et al., *Science,* 252, 802–808 (1991). Briefly, G proteins are heterotrimeric proteins (each having an α, β, and γ subunit) which mediate signal transduction in olfactory, visual, hormonal and neurotransmitter systems. G proteins couple cell surface receptors to cellular effector enzymes (e.g., phosphodiesterases and adenylate cyclase) and thereby transduce an extracellular signal into an intracellular second messenger (e.g., cAMP, cGMP, $IP_3$). The α subunit of a G protein confers most of the specificity of interaction between its receptor and its effectors in the signal transduction process, while β and γ subunits appear to be shared among different G proteins. Some G proteins are ubiquitously expressed (e.g., $G_s$ and $G_i$), but others that are known to be involved in sensory transduction have been found only in specialized sensory cells. For example, the transducins ($G_t$) transduce photoexcitation in retinal rod and cone cells [see Lerea et al., *Science,* 224, 77–80 (1986)], and $G_{olf}$ transduces olfactory stimulation in neurons of the olfactory epithelium [see Jones et al., *Science,* 244, 790–795 (1989)]. The ubiquitously expressed G proteins may also be involved in sensory transduction.

While no direct evidence for the existence of a gustatory specific G protein has been previously reported, experimental data suggesting that G proteins are involved in the taste transduction pathway is described in several publications, including, for example, the reviews of Kinnamon et al., *TINS,* 11(11), 491–496 (1988); Avenet et al., *J. Membrane Biol.,* 112, 1–8 (1989); and Roper, *Ann. Rev. Neurosci.,* 12, 329–353 (1989).

Avenet et al., *Nature,* 331, 351–354 (1988) and Tonosaki et al., *Nature,* 331, 354–356 (1988) report that external application or microinjection of cAMP inactivates potassium channels in vertebrate taste cells and leads to depolarization of these cells. Kurihara et al., *Biophys. Res. Comm.,* 48, 30–34 (1972) and Price et al., *Nature,* 241, 54–55 (1973) describe high levels of adenylyl cyclase and cAMP phosphodiesterase in taste tissue.

In Striem et al., *Biochem. J.,* 260, 121–126 (1989), sweet compounds are proposed to cause a GTP-dependent generation of cAMP in rat tongue membranes. These results suggest a transduction pathway in which tastant interaction with a sweet receptor leads to taste cell depolarization via a G protein mediated rise in cAMP. Akabas et al., *Science,* 242, 1047–1050 (1988) reports that bitter compounds such as denatonium lead to $Ca^{2+}$ release from internal stores. The release may be a result of G protein-mediated generation of inositol triphosphate ($IP_3$). Thus, bitter taste may also be transduced via a G protein.

Over the past decade substantial efforts have been directed to the development of various agents that interact with taste receptors to mimic or block natural taste stimulants. See, Robert H. Cagan, Ed., *Neural Mechanisms in Taste,* Chapter 4, CRC Press, Inc., Boca Raton, Fla. (1989). Examples of agents that have been developed to mimic sweet tastes are saccharin (an anhydride of o-sulfimide benzoic acid) and monellin (a protein) and the thaumatins (also proteins). Thaumatins have been utilized as additives in food, cigarette tips, medicines and toothpaste [see Higginbotham et al, pp. 91–111 in *The Quality of Foods and Beverages,* Academic Press (1981)]. Many taste-mimicking or taste-blocking agents developed to date are not suitable as food additives, however, because either they are not economical or are high in calories, or because they are carcinogenic. Development of new agents that mimic or block the four basic tastes has been limited by a lack of knowledge of the taste cell proteins responsible for transducing the taste modalities. There thus continues to exist a need in the art for new products and methods that are involved in or affect taste transduction.

SUMMARY OF THE INVENTION

The present invention provides products and methods that are involved in or that affect taste transduction. In one of its aspects, the present invention provides purified and isolated polynucleotide sequences (e.g., DNA sequences and RNA transcripts thereof) encoding the α subunit of a novel taste receptor cell specific G protein, gustducin, or fragments and variants of the α subunit that possess at least one ligand/antiligand binding activity or immunological property specific to gustducin. Preferred polynucleotide sequences of the invention include genomic and cDNA sequences as well as wholly or partially synthesized DNA sequences, and biological replicas thereof. Biologically active vectors comprising the polynucleotide sequences are also contemplated.

The scientific value of the information contributed through the disclosures of the DNA and amino acid sequences of the present invention is manifest. For example, knowledge of the sequence of a cDNA encoding the gustducin α subunit makes possible the isolation by DNA/DNA hybridization of genomic DNA sequences that encode the subunit and that specify α subunit-specific expression regulating sequences such as promoters, operators and the like. DNA/DNA hybridization procedures utilizing the DNA sequences of the present invention also allow the isolation of DNAs encoding heterologous species proteins homologous to the rat gustducin α subunit specifically illustrated herein, such as human species gustducin α subunit protein.

According to another aspect of the invention, host cells, especially unicellular eucaryotic and procaryotic cells, are stably transformed or transfected with the polynucleotide sequences of the invention in a manner allowing the expression of gustducin α subunit polypeptides in the cells. Host cells expressing gustducin α subunit polypeptide products, when grown in a suitable culture medium, are particularly useful for the large scale production of gustducin α subunit polypeptides, fragments and variants; thereby enabling the isolation of the desired polypeptide products from the cells or from the medium in which the cells are grown.

The novel gustducin α subunits, fragments and variants of the invention may be obtained as isolates from natural taste cell sources, but are preferably produced by recombinant procedures involving the host cells of the invention. The products may be obtained in fully or partially glycosylated, partially or wholly de-glycosylated or non-glycosylated forms, depending on the host cell selected or recombinant production and/or post-isolation processing. Similarly, the products may be obtained in fully or partially myristoylated, partially or wholly de-myristoylated or non-myristoylated forms, also depending on the host cell selected or recombinant production and/or post-isolation processing.

Gustducin α subunit variants according to the invention may comprise polypeptide analogs wherein one or more of the specified amino acids is deleted or replaced or wherein one or more nonspecified amino acids are added: (1) without loss, and preferably with enhancement, of one or more of the biological activities or immunological characteristics specific for gustducin; or (2) with specific disablement of a particular ligand/antiligand binding function.

Also contemplated by the present invention are antibody substances (e.g., monoclonal and polyclonal antibodies, chimeric and humanized antibodies, and antibody domains including Fab, Fab', $F(ab')_2$ and single chain domains, and Fv or single variable domains) which are specific for the gustducin α subunit. Antibody substances can be developed using isolated natural or recombinant gustducin α subunit polypeptide products or host cells expressing such products on their surfaces. The antibody substances may be utilized for purifying polypeptides of the invention and for blocking or inhibiting ligand/antiligand binding activities of gustducin.

Yet another aspect of the present invention relates the observation that gustducin α subunit polypeptides (and by virture of their sequence homology to gustducin, rod or cone transducin α subunit polypeptides) are particularly suited for use in methods for identifying taste modifying agents. Methods of identifying taste modifying agents according to the invention generally involve testing an agent for the capability to mimic or inhibit the interaction of gustducin α subunit with a sensory receptor or for the capability to mimic or inhibit the interaction of gustducin α subunit with an effector enzyme.

A first preferred method for identifying a taste modifying agent comprises the steps of incubating phospholipid vesicles having gustducin α subunit or transducin α subunit and G protein β and γ subunits associated in biologically active form with an agent and with radioactively labeled GTPγS, and determining the rate of GTPγS binding by the α subunit in comparision to a standard rate. An increase in the rate of binding indicates that the agent is a taste stimulator and a decrease in the rate of binding indicates that the agent is a taste inhibitor.

A second preferred method for identifying a taste modifying agent includes the steps of incubating phospholipid vesicles having gustducin α subunit or transducin α subunit and G protein β and γ subunits associated in biologically active form with a particular agent and radioactively labeled GTP, and determining the rate of conversion of GTP to GDP by the α subunit in comparison to a standard rate. An increase in the rate of conversion indicates that the agent is a taste stimulator and a decrease in the rate of conversion indicates that the agent is a taste inhibitor.

A third preferred method for identifying a taste inhibiting agent comprises the steps of incubating activated gustducin α subunit or activated transducin α subunit with an agent and a phosphodiesterase, and measuring phosphodiesterase activation by the α subunit in comparison to a standard. A decrease in phosphodiesterase activity indicates that the agent is a taste inhibitor.

A fourth preferred method for identifying a taste modifying agent includes the steps of incubating washed disk membranes (e.g., from bovine retina) with gustducin α subunit or transducin α subunit associated with G protein β and γ subunits in biologically active form with a particular agent, subjecting the membranes to photolyzing conditions (i.e., 532 nm light), and determining absorption of photolytic reaction products at 380 nm in comparison to a standard. An increase in absorption at 380 nm indicates that the agent is a taste stimulator and a decrease in absorption at 380 nm indicates that the agent is a taste inhibitor.

Taste modifying agents may, for example, comprise a peptide possessing at least one ligand/antiligand binding activity specific to the α subunit of gustducin. Amino acid sequences of presently preferred taste modifying peptides are set out in SEQ ID NOs: 1–10, wherein SEQ ID NOs: 1–3 correspond to the carboxyl terminal region of rat gustducin α subunit, SEQ ID NOs: 4–7 correspond to the carboxyl terminal portion of bovine transducin and SEQ ID NOs: 8–10 correspond to loop peptides of bovine rhodopsin. Taste modifying peptides may be acetylated at the amino terminus or amidated at the carboxyl terminus.

Other peptide ligands/antiligands of the gustducin α subunit may be identified by contacting gustducin α subunits with peptides and isolating the peptides which bind to the subunits. Appropriate peptide display libraries or phage epitope libraries which may be utilized in such methods are described in Scott et al., *Science*, 249, 386–390 (1990); Lam et al., *Nature*, 354, 82–84 (1991); and Houghton et al., *Nature*, 354, 84–86 (1991).

According to another aspect of the present invention, taste modifying agents such as peptides having a ligand/antiligand binding activity of gustducin α subunit or an antibody substance specific for gustducin α subunit are delivered to taste receptor cells to modify taste (e.g., mimic or inhibit sweet and/or bitter tastes).

Numerous aspects and advantages of the present invention will be apparent upon consideration of the following illustrative examples and descriptions.

BRIEF DESCRIPTION OF THE FIGURES

FIGS. 1A through C sets out the DNA and deduced amino acid sequences of the α subunit of rat species gustducin (SEQ ID NOs: 11 and 12).

FIGS. 2A–2B is an alignment of amino acid sequence of the α subunits of rat gustducin (SEQ ID NO: 12), bovine cone transducin (cone) (SEQ ID NO: 13), bovine rod transducin (rod) (SEQ ID NO: 14) and a consensus sequence (SEQ ID NO: 15) derived from the alignment of the three α subunits, wherein capital letters in the consensus sequence indicate that all three subunits have the same amino acid at that position, lower-case letters indicate that two of the three proteins have the same and no acid at that position, and dots indicate that all three subunits have a different amino acid at that position.

DETAILED DESCRIPTION

The present invention is illustrated by the following examples wherein Example i describes the cloning and characterization of DNA sequences encoding the α subunit of rat species gustducin, Example 2 describes experiments relating to the expression of the α subunit of gustducin, and Example 3 describes methods for identifying taste modifying agents having the capability to affect interactions between the gustducin α subunit and taste receptors or effectors and also describes methods for utilizing such taste modifying agents to modify taste by mimicking or inhibiting sweet, bitter, salty or sour tastes.

EXAMPLE 1

A cDNA clone encoding a heretofore unknown taste cell specific G protein was isolated by PCR from a taste cell enriched cDNA library. Taste buds were estimated to comprise 10–30% of the total mass of taste tissue harvested to make the library. In contrast, taste buds represent less than 1% of the total lingual epithelium. A control cDNA library was made from lingual epithelium devoid of taste buds.

Construction of cDNA Libraries

The circumvallate and foliate papillae from ninety Sprague-Dawley rats were harvested by the method described in Spielman et al., *Chem. Senses,* 14, 841–846 (1989) and immediately frozen in 100% ETOH at −70° C. An equivalent amount of non-taste lingual epithelium (devoid of taste buds) was likewise harvested. Poly A+ mRNA was isolated from taste and non-taste lingual tissue using a Quick Prep kit (Pharmacia, Upsala, Sweden). 7.9 μg of mRNA was recovered from the taste tissue and 2.4 μg of mRNA was recovered from the control non-taste lingual tissue. The Superscript kit (BRL, Bethesda, Md.), which utilizes the pSPORT vector, was used to make two cDNA libraries from 1 μg of taste and 1 μg of non-taste lingual mRNA. The taste library contained $2.6\times10^6$ independent clones (average insert size of 1.1 kb). The non-taste library contained $4.8\times10^6$ independent clones (average insert size of 1.0 kb).

Design and Sythesis of PCR Primers

Six degenerate oligonucleotide primer sets were made that corresponded to regions of amino acids highly conserved among previously described G protein α subunits including $\alpha_s$, $\alpha_{olf}$, $\alpha_{i-1,3}$, $\alpha_{i-2}$, $\alpha_o$, $\alpha_z$, $\alpha_q$, $\alpha_{t\text{-}rod}$, and $\alpha_{t\text{-}cone}$ subunits. The amino acid sequences of the conserved regions and the DNA sequences (in IUPAC nomenclature) of the corresponding degenerate primer sets, which were synthsized on an Applied Biosystems DNA synthesizer, are set out below. Oligonucleotides corresponding to 3' primers (sets 2, 4, and 6) were synthesized in the antisense orientation. Underlined sequences at the end of each oligonucleotide contain a restriction endonuclease site (BamH1 for oligonucleotides used as 5' primers and EcoR1 oligonucleotides used as 3' primers) to facilitate cloning. The nucleotide number (Nuc. #) in parentheses refers to the gustducin α subunit nucleotide location now known to correspond to the first amino acid of the primer.

Set 1

KWIHCF (Nuc. 741) (SEQ ID NO: 16)
5' CGGATCCAARTGGATHCAYTGYTT 3' (SEQ ID NO: 17)

Set 2

FLNKKD (Nuc. 912) (SEQ ID NO: 18)
5' GGAATTCRTCYTTYTTRTTNAGRAA 3' (SEQ ID NO: 19) and
5' GGAATTCRTCYTTYTTRTTYAARAA 3' (SEQ ID NO: 20)

Set 3

DVGGQR (Nuc. 711) (SEQ ID NO: 21)
5' GTCTAGAGAYGTNGGNGGNCARMG 3' (SEQ ID NO: 22)

Set 4

VFDAVTD (Nuc. 1116) (SEQ ID NO: 23)
5' CCGAATTCTCNGTNACNGCRTCRAANAC 3' (SEQ ID NO: 24)

Set 5

TIVKQM (Nuc. 255) (SEQ ID NO: 25)
5' CCGAATTCACNATNGTNAARCARATG 3' (SEQ ID NO: 26)

Set 6

FLNKQD (Nuc. 912) (SEQ ID NO: 27)
5' CCGAATTCRTCYTGYTTRTTNARRAA 3' (SEQ ID NO: 28)

Primer sets 1, 2 and 3 were previously described in Strathmann et al., *Proc. Natl. Acad. Sci. USA,* 86, 7407–7409 (1990). The two degenerate oligonucleotides comprising set 2 were always used together in equimolar amounts.

Cloning of cDNA Encoding the Gustducin α Subunit by PCR

DNA from the taste cell library was used as a substrate for PCR using several pairwise combinations of two of the foregoing degenerate primer sets: 1 and 2, 2 and 3, and 5 and 6. PCR samples contained 250 pmol of each primer, 20 ng of taste cell library cDNA, and 1 unit pyrostase (Molecular Genetic Resources, Tampa, Fla.) in a 50 μl reaction volume. The PCR program was: 94° for 1 minute, 37° to 72° with a rise time of 1° per 4 seconds, then 72° for 3 minutes for three cycles; followed by 94° for 1 minute, then 43° for 2 minutes, and finally 72° for 3 minutes for a total of 35 additional cycles. The PCR products were digested with BamHI and EcoRI, and electrophoresed in a 1% agarose gel. Bands of expected size were excised, purified, cloned into the pBluescript vector (Stratagene, La Jolla, Califa.), and transformed into *E. coli.* Individual colonies were picked, and the DNA isolated therefrom was sequenced.

Partial clones were categorized according to α subtype specificity based on their deduced amino acid sequence. Eight different types of α subunit clones were isolated. Seven of the α subunit types ($\alpha_s$, two types of $\alpha_i$, two types of $\alpha_q$, and two types of $\alpha_t$) had been previously identified and are expressed in tissues other than lingual epithelium. The eighth type of clone (generated in PCR reaction using primer sets 1 and 2, and 5 and 6) was a novel G protein α subunit clone. This gustatory clone was one of the most frequent isolates, suggesting that it is present in relatively high abundance in the taste tissue cDNA library.

To determine the complete sequence of the gustatory α subunit clone both further PCR reactions and colony hybridization to the taste cell cDNA library using PCR products as probes were performed.

PCR reactions were performed as described above using the α subunit specific primer set out below (which was synthesized in the antisense orientation and has a BamH1 site at its 5' end) and degenerate primer set 4.

HLFNSIC (Nuc. 855) (SEQ ID NO: 29)
5' CCGGATCCGCACCTGTTCAACAGCATCT 3' (SEQ ID NO.: 30)

The PCR fragments generated were cloned and sequenced as described above.

Nested PCR reactions using the α subunit specific primers indicated below were performed to obtain gustatory α subunit 5' sequences.

KYFATTS (Nuc. 882) (SEQ ID NO: 31)
CCGGATCCGAGGTGGTTGCAAAATACTT (SEQ ID NO: 32)
LAEIIKR (Nuc. 480) (SEQ ID NO: 33)
CGGATCCGACGTTTAATTATTTCAGCCAA (SEQ ID NO: 34)

The primer set out in SEQ ID NO: 32 and a T7 sequencing primer (BRL), which corresponds to the T7 promoter region of the pSPORT vector containing the taste cell library, were used as primers in a first PCR reaction. Next, the PCR fragments generated were reamplified using the primer set out in SEQ ID NO: 34 and the T7 sequencing primer (BRL). The reamplfied fragments were then cloned and sequenced as described above.

A PCR fragment amplified using primer set 5 and the primer set out in SEQ ID NO: 32 was used as a probe for colony hybridizations to the rat taste cell cDNA library to obtain/confirm the gustatory α subunit sequence. Clones designated T95, T93, T85 and T77 were isolated and sequenced.

A composite gustatory α subunit clone was assembled in the plasmid vector pSPORT (BRL) and the resulting plasmid was designated pSPORT-gustducin. Clone T95 (comprising the pSPORT vector and gustatory α subunit sequences) was digested with NsiI (an endonuclease which does not cut within the pSPORT vector, but cuts at two sites within the α subunit DNA at nucleotides 354 and 886) to yield two fragments. The larger fragment (~5250 bp containing pSPORT vector sequences and most of the gustatory α subunit sequences) was recovered after being isolated away from the smaller fragment (~400 bp). A fragment containing the remaining gustatory α subunit sequences was derived from PCR amplification of the taste cell cDNA library with primer set 5 and the gustatory α subunit specific primer set out in SEQ ID NO: 32. The PCR product generated was digested with NsiI, resulting in a 532 bp fragment. The 532 bp fragment was then ligated to the large fragment isolated from clone T95 to generate a composite α subunit clone in the vector pSPORT. The 5' end of the gustatory α subunit cDNA is coupled to sequences derived from a SalI/MluI adaptor used to make the original cDNA library in the vector pSPORT (vector . . . 5' TCGACCCACGCGTCCG 3'/5'gustducin) [i.e., vector . . . (SEQ ID NO: 35)/ 5'gustducin). The 3' end of the gustducin cDNA is coupled to the T-tailed NotI primer-adapter used in the original pSPORT library construction (gustducin 3'/5' GGGCGGCCGC 3' . . . vector) [i.e., gustducin 3'/(SEQ ID NO: 37) . . . vector].

The DNA and deduced amino acids sequences of the composite gustatory α subunit clone are respectively set out in SEQ ID NOs: 11 and 12, and in FIGS. 1A through 1C. The gustatory α subunit sequence consists of 1703 bp of DNA with a single long open reading frame sufficient to encode a protein of 354 amino acids. It contains potential sites for pertussis toxin ($C_{351}$) and cholera toxin ($R_{178}$) mediated ribosylation.

Comparison of the Sequence of the Gustatory α Subunit Clone with Known G Protein α Subunits The Tfasta and Fasta programs of the Wisconsin GCG software package described in Devereaux et al., *Nucl. Acids Res.*, 12,387–395 (1984), were used to search GenBank for DNA and amino acid sequences related to the α subunit of rat gustatory protein. The search revealed that the α subunit is a member of the $\alpha_i$ superfamily and is most closely related to the bovine rod and bovine cone transducins. Due to its close relationship to the transducins and its presumptive role in taste transduction, the gustatory G protein was named gustducin. At the amino acid level, the α subunit of rat gustducin is 80% identical and 90% similar to the α subunit of bovine rod transducin, and is 79% identical and 90% similar to the α subunit of bovine cone transducin. In comparison, bovine rod α transducin is 81% identical and 90% similar to bovine cone α transducin. Since the rat transducin α subunit DNA sequences have not been determined, a comparison of rat gustducin α subunit to rat transducin α subunits could not be made. However, among mammals, a 1 to 3% difference in amino acid identity is typical among α isotypes, suggesting that the α subunits of gustducin and the transducins comprise a subfamily of closely related proteins. In contrast, gustducin α subunit is only about 67% identical to the $\alpha_i$ subunits, and only 46% identical to $\alpha_s$ subunits (similar levels of homology exist between the transducins and $\alpha_i$ or $\alpha_s$).

An alignment of gustducin α subunit with the α subunits of bovine rod and cone transducin produced iteratively by the BestFit routine of the Wisconsin GCG software package (Devereaux et al., supra) shows that the general structure of all three α subunits is highly conserved (see FIGS. 2A through 2B). The amino terminal 60 amino acids and the carboxyl terminal 60 amino acids of all three proteins are highly conserved, while the carboxyl terminal 38 amino acids are identical. This carboxyl terminal identity is of particular importance because it encompasses the site that has been implicated in G protein/receptor interactions. Moreover, the region from $Q_{137}$ through $F_{354}$ is extremely similar for all three subunits; each α subunit has only 14 or 15 differences from the consensus sequence in this region. This region contains most of the sites implicated in guanine nucleotide binding. Amino acids $G_{42}$, $R_{197}$ and $Q_{204}$ regulate GTPase activity and are present in all three proteins. These comparisons suggest that the guanine nucleotide binding properties and GTPase activities of these three α subunits are likely to be quite similar. All three α subunits contain a potential N-myristoylation site at their terminus which, if utilized, may anchor these α subunits to the inner face of the plasma membrane. Most differences among the three proteins are clustered in the region from $V_{96}$ to $S_{109}$ of gustducin, which is a highly variable region of G protein α subunits.

Gustducin α Subunit is a Single Copy Gene

Although the α subunit of gustducin is closely related to the transducin α subunits, it differs at the amino acid level at several positions scattered throughout its sequence. This suggests that α gustducin is transcribed from a gene distinct from the transducins. Southern blot analysis with gustducin α subunit probes vs. transducin α subunit probes confirmed that gustducin is a single copy gene with a distinct restriction endonuclease digestion pattern.

Splicing Variants of Gustducin α Subunit

In screening the taste enriched cDNA library two apparent splicing variants of the α subunit of gustducin were found. One type of clone (T95) contained the entire coding region of the gustducin α subunit, but had an in frame deletion of 135 bp. When this cDNA sequence is aligned with the genomic sequence of the α subunit of murine transducin, the deletion corresponds to the precise removal of the sixth exon. The general exon-intron organization of G protein α subunits is highly conserved, therefore it is likely that the "deletion" in clone T95 corresponds to splicing out of gustducin exon 6.

Another type of clone (T93, T85 and T77) from the cDNA library contained an insertion of 193 bp. Comparison with the sequence of the exon/intron boundaries of the genomic clone of murine transducin α subunit indicates that this insertion is due to the presence of an unspliced intron between exons 6 and 7.

PCR reactions using primers spanning exons 6 and 7 showed that the abberantly spliced (deleted) variant and the unspliced form are present in taste-enriched cDNA at levels approximately one tenth that of the correctly spliced α gustducin cDNA. The amino acids present within exon 6 ($R_{197}$ to $N_{241}$) are highly conserved for $\alpha_i$ subunits and transducin α subunits and have been implicated in guanine nucleotide binding. If the deleted form of gustducin is actually produced it would differ significantly in its guanine nucleotide binding properties and GTPase activities from other α proteins. The unspliced form of gustducin would produce a truncated protein lacking the terminal 114 amino acids, which would also be altered in its guanine nucleotide binding properties and in its ability to interact with receptors if produced.

Transducin in Taste Cells

Interestingly, transducin α subunit cDNAs (both rod and cone) were isolated by PCR amplification of the taste cell library. Furthermore, transducin α subunit mRNA was shown to be present in taste buds by RNase protection assays and by in situ hybridization. This was the first demonstration of the presence of transducin in a tissue other than the photoreceptor cells of the retina. Transducin may therefore participate in taste transduction as well as visual transduction.

EXAMPLE 2

Expression of gustducin α subunit mRNA was assayed by Northern blot, primer extension and RNase protection.

Expression Products (mRNA) of the Gustducin α Subunit

Northern blot analysis of poly A+ mRNA from taste tissue using labeled gustducin α subunit DNA as a probe indicates three transcripts: a closely spaced doublet ~1700–1800 nt and a faint third hand ~1500 nt. The products of primer extension reactions using cRNA (i.e., RNA generated in vitro as run-off transcripts from the taste cell cDNA library) as template and gustducin specific primers indicated the same 5' terminus as indicated in FIGS. 1A through 1C. These results indicate that the full length α gustducin clone is ~1700 nt in length as depicted in FIGS. 1A through 1C.

Tissue Expression of the Gustducin α Subunit

Tissue specific expression of gustducin α subunit transcripts was assayed by RNase protection. The template RNAs used for RNase protection were total RNA or, in those cases in which abundant RNA was not readily available, cDNA libraries were made from poly A+ mRNA, then cRNA was made from the libraries. RNase protection was done simultaneously with gustducin α subunit probes and actin probes to normalize for expression. All RNAse protection assays were done using a RNase protection kit (Ambion, Austin, Tex.) according to the method described in Krieg et al., *Methods Enz.*, 155, 397–415 (1987).

The RNase protection assays demonstrated the presence of gustducin α subunit RNA only in taste tissue enriched preparations. No α subunit RNA was detected in the non-taste lingual tissue, olfactory epithelium, retina, brain, liver, heart or kidney.

In situ hybridization using labeled gustducin α subunit RNA probes demonstrated the presence of α gustducin mRNA in the taste buds of circumvallate, foliate, and fungiform papillae, tissues directly involved in taste transduction. Gustducin mRNA was completely absent from lingual tissue not involved in taste transduction including non-sensory lingual epithelium, muscle, connective tissue and von Ebner's glands.

Gustducin α Subunit Expression Requires Afferent Innervation

To determine if the expression of gustducin α subunit mRNA is dependent on the presence of taste buds, in situ hybridizations using labeled gustducin α subunit antisense RNA as probes were carried out on frozen sections taken from rats whose tongues had been denervated. When the nerves innervating taste buds are severed, the buds degenerate and do not reappear unless the connections are restored. If gustducin α subunit mRNA is present only within the taste buds, it follows that upon degeneration of the taste buds, gustducin α subunit would no longer be expressed.

In the rat, taste buds are innervated by branches of the glossopharyngeal, the facial, and the vagal cranial nerves. The glossopharyngeal nerve innervates the circumvallate papilla, and some taste buds of the foliate papillae. The chorda tympani innervates the foliate papillae as well as the fungiform papillae of the anterior portion of the tongue.

Two types of denervation were performed: (a) bilateral section of both glossopharyngeal nerves and (b) unilateral section of the left glossopharyngeal nerve and the left chorda tympani. The circumvallate papilla is innervated only by the glossopharyngeal nerves; bilateral sectioning of these nerves causes the taste buds of this papilla to degenerate. Unilateral sectioning causes the taste buds of the ipsilateral foliate papilla to degenerate, but leaves the taste buds of the contralateral foliate papilla intact. Fourteen days post-surgery (to allow full degeneration of taste buds) tissue sections containing foliate and circumvallate papillae were subjected to in situ hybridization with α gustducin anti-sense probe.

Following bilateral glossopharyngeal denervation the circumvallate papilla was totally devoid of taste buds and gustducin α subunit mRNA expression was likewise absent from the circumvallate papilla. As expected, taste buds expressing α gustducin mRNA were still present in the foliate papillae of these rats (since input from the chorda tympani remained). However, the number of taste buds in these papillae did appear to be reduced. Following unilateral sectioning of the left chorda tympani and left glossopharyngeal nerve, the ipsilateral foliate papilla was devoid of taste buds and displayed no detectable expression of gustducin α subunit mRNA, however, the contralateral foliate papilla retained taste buds which did express gustducin α subunit mRNA. These results directly correlate the presence of innervated taste buds with gustducin α subunit expression.

EXAMPLE 3

Based on the amino acid sequence homology between the gustducin α subunit and the transducin α subunits and on the taste cell specific expression pattern of both the gustducin α subunit and the transducin α subunit, it is reasonable to conclude that the roles of gustducin and transducin in taste transduction is similar to the role of transducin in the visual system. Gustducin and/or transducin are likely to transduce taste receptor activation into activation or inhibition of a taste cell effector such as cAMP or cGMP phosphodiesterase. Gustducin α subunits and transducin α subunits may therefore be utilized in methods to identify taste modifying agents that are capable of mimicking, blocking or inhibiting particular tastes. As indicated below, the specific identification methods are designed by analogy to procedures employed to characterize activation and effector functions of known G proteins.

A first type of method identifies taste modifying agents that mimic or block the effect of an activated taste receptor on the gustducin or transducin α subunit. For example, one method contemplated by the invention is analogous to an assay described in Cheung et al., *FEBS Letters*, 279(2), 277–280 (1991) wherein evidence of peptide activation of various G proteins was an increase in the rate of GTPγS binding by G protein α subunits. (GTPγS is a nonhydrolyzable form of GTP.) The method therefore may include the steps of incubating phospholipid vesicles having gustducin α subunit (bound to GDP) or transducin α subunit (bound to GDP) and G protein β and γ subunit (i.e., any purified β and γ subunits may be used) associated in biologically active form with a putative taste modifying agent and radioactively labeled GTPγS, and determining the rate of GTPγS binding by the α subunit in comparision to a standard rate (i.e., the rate of binding in the absence of the agent). An increase in the rate of binding indicates that the agent is a taste stimulator and a decrease in the rate of binding indicates that the agent is a taste inhibitor.

Another method of the first type is analogous to a different assay described in Cheung et al., *FEBS Letters*, 279(2), 277–280 (1991) wherein evidence of peptide activation of various G proteins was an increase in the rate of G protein α subunit GTPase activity. This method may therefore comprise the steps of incubating phospholipid vesicles having gustducin α subunit (bound to GDP) or transducin α subunit (bound to GDP) and G protein β and γ subunit associated in biologically active form with a putative taste modifying agent and radioactively labeled GTP, and determining the rate of conversion of GTP to GDP by the α subunit in comparison to the rate of conversion in the absence of the agent. An increase in the rate of conversion indicates that the agent is a taste stimulator and a decrease in the rate of conversion indicates that the agent is a taste inhibitor.

Yet another method of the first type contemplated by the invention is analogous to an assay described in König et al., *Proc. Natl. Acad Sci. USA*, 86, 6878–6882 (1989) wherein evidence for transducin α subunit interaction with an activated receptor (rhodopsin) is an increase in absorbance at 380 nm. (It is likely that gustducin will interact with rhodopsin because the carboxyl terminal thirty-eight amino acids of transducin [which have been shown to include the site of transducin interaction with rhodopsin, see Nishizuka et al., Eds., pp. 76–82 in *The Biology and Medicine of Signal Transduction*, Raven Press, New York (1990)] are identical to the carboxyl terminal thirty-eight amino acids of gustducin. The method includes the steps of incubating washed disk membranes having gustducin α subunit (bound to GDP) or transducin α subunit (bound to GDP) associated with G protein β and γ subunits in biologically active form with a putative taste modifying agent, subjecting the incubation mixture to photolyzing conditions (i.e., 532 nm light), and determining absorption at 380 nm (vs. 417 nm) in comparison to absorption in the absence of the agent. An increase in absorption at 380 nm indicates the agent is a taste stimulator and a decrease in absorption at 380 nm indicates that the agent is a taste inhibitor.

A second type of method identifies taste modifying agents that mimic or block the effect of activated gustducin or transducin α subunit (i.e., subunit having bound GTP or GTPγS) on an effector. A contemplated method of this type is analogous to an assay described in Beavo et al., Eds., Chpt. 7 in *Cyclic Nucleotide Phosphodiesterases: Structure, Regulation and Drug Action*, John Wiley and Sons Ltd. (1990), wherein phosphodiesterase (PDE) activation is evidence of transducin interaction with an effector, cGMP PDE. The method therefore may include the steps of incubating activated gusducin α subunit or activated transducin α subunit with a putative taste modifying agent and cAMP (or cGMP) PDE, and measuring phosphodiesterase activation by the α subunit in comparison to the level of phosphodiesterase activity in the absence of the agent. A decrease in activity indicates that the agent is a taste inhibitor.

Peptides (e.g., fragments of antibodies to gustducin or transducin and peptides corresponding to portions of gustducin or transducin) that mimic or compete with a binding activity of the gustducin or transducin α subunits may be taste modifying agents. These peptides are likely to affect the interaction of the gustducin/transducin α subunits with sensory receptors, cellular effectors and/or their associated β and γ subunits. Examples of amino acid sequences of such taste modifying peptides are: SEQ ID NOs: 1–3, which correspond to the carboxyl terminal region of rat gustducin α subunit; SEQ ID NOs: 4–7, which correspond to the carboxyl terminal portion of bovine transducin; and SEQ ID NOs: 8–10, which correspond to loop peptides of bovine rhodopsin.

Antibody substances (including monoclonal and polyclonal antibodies, chimeric and humanized antibodies, and antibody domains including Fab, Fab', $F(ab')_2$ and single chain domains, and Fv or single variable domains) that are specific for the gustducin α subunit may be developed using isolated natural or recombinant gustducin α subunit polypeptide products or host cells expressing such products on their surfaces. The antibody substances may be utilized for blocking or inhibiting the ligand/antiligand binding activities of gustducin as described in the foregoing paragraph and for purifying gustducin materials of the invention.

While the present invention has been described in terms of preferred embodiments, it is understood that variations and improvements will occur to those skilled in the art. Therefore, it is intended that the appended claims cover all such equivalent variations which come within the scope of the invention as claimed.

What is claimed is:

1. A purified and isolated gustducin α subunit polynucleotide consisting of the nucleotide sequence set out in SEQ ID NO: 11.

2. A purified and isolated polynucleotide encoding a gustducin α subunit polypeptide consisting of the amino acid sequence set out in SEQ ID NO: 12.

3. A biologically functional DNA vector comprising a polynucleotide according to claim 1 or 2.

4. A host cell stably transformed or transfected with a polynucleotide according to claim 1 or 2.

5. A method for producing gustducin α subunit polypeptide comprising the steps of growing a host cell according to claim 4 in a suitable nutrient medium and isolating gustducin α subunit polypeptide from said cell or the medium of its growth.

* * * * *

UNITED STATES PATENT AND TRADEMARK OFFICE

CERTIFICATE OF CORRECTION

PATENT NO. : 5,688,662

DATED : November 18, 1997

INVENTOR(S) : Robert F. Margolskee

It is certified that error appears in the above-identified patent and that said Letters Patent is hereby corrected as shown below:

Column 5, line 24 replace "Example i" with --Example 1--;

Column 12, line 3 replace "gustducin." with --gustducin.)--;

Signed and Sealed this

Eighteenth Day of January, 2000

Attest:

Q. TODD DICKINSON

*Attesting Officer* *Commissioner of Patents and Trademarks*

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Glu Asp Lys Glu Ile Tyr Ser His Met Thr Cys Ala Thr Asp Thr Gln
1               5                   10                  15

Asn Val
```

( 2 ) INFORMATION FOR SEQ ID NO:2:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Glu Asp Lys Glu Ile Tyr Ser His Met Thr Cys Ala Thr Asp Thr Gln
1               5                   10                  15

Asn Val Lys
```

( 2 ) INFORMATION FOR SEQ ID NO:3:

( i ) SEQUENCE CHARACTERISTICS:
( A ) LENGTH: 40 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Glu Asp Lys Glu Ile Tyr Ser His Met Thr Cys Ala Thr Asp Thr Gln
1               5                   10                  15

Asn Val Lys Phe Val Phe Asp Ala Val Thr Asp Ile Ile Ile Lys Glu
            20                  25                  30

Asn Leu Lys Asp Cys Gly Leu Phe
        35                  40
```

( 2 ) INFORMATION FOR SEQ ID NO:4:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:4:

```
Glu Glu Lys His Ser Arg Glu Leu Glu Lys Lys Leu Lys Glu Asp Ala
1               5                   10                  15

Glu Lys Asp Ala Arg
            20
```

( 2 ) INFORMATION FOR SEQ ID NO:5:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:5:

```
Asp Val Lys Glu Ile Tyr Ser His Met Thr Cys Ala Thr Asp Thr Gln
1               5                   10                  15

Asn Val
```

( 2 ) INFORMATION FOR SEQ ID NO:6:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO:6:

```
Asp Val Lys Glu Ile Tyr Ser His Met Thr Cys Ala Thr Asp Thr Gln
1               5                   10                  15

Asn Val Lys
```

( 2 ) INFORMATION FOR SEQ ID NO:7:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:7:

```
Ile Lys Glu Asn Leu Lys Asp Cys Gly Leu Phe
1               5                   10
```

( 2 ) INFORMATION FOR SEQ ID NO:8:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( x i ) SEQUENCE DESCRIPTION: SEQ ID NO:8:

```
Lys Pro Met Ser Asn Phe Arg Phe Gly Glu Asn His Ala
1               5                   10
```

( 2 ) INFORMATION FOR SEQ ID NO:9:

( i ) SEQUENCE CHARACTERISTICS:
( A ) LENGTH: 23 amino acids
( B ) TYPE: amino acid
( D ) TOPOLOGY: linear ( i i ) MOLECULE TYPE: peptide ( x i ) SEQUENCE DESCRIPTION: SEQ ID NO:9:

```
Val Lys Glu Ala Ala Ala Gln Gln Gln Glu Ser Ala Thr Thr Gln Lys
1               5                   10                  15

Ala Glu Lys Glu Val Thr Arg
```

2 0

( 2 ) INFORMATION FOR SEQ ID NO:10:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Asn Lys Gln Phe Arg Asn Cys Met Val Thr Thr Leu
1 5 10

( 2 ) INFORMATION FOR SEQ ID NO:11:

( i ) SEQUENCE CHARACTERISTICS:
( A ) LENGTH: 1703 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

GACTGGTGCC TGCTGTTGGG AGCACTGCTC TGACGATCTA TCTCTAAACC ACTGCTGTGC 60

TCTGTGTTTG AAAACTTTGA GCAAATCAAC TGCCCGTCCT CTAACAGCAA AAGATGGGAA 120

GTGGAATTAG TTCAGAGAGC AAGGAGTCAG CCAAAAGGTC CAAAGAACTG GAGAAGAAGC 180

TTCAGGAAGA TGCTGAACGA GATGCAAGAA CTGTGAAGTT GCTGCTATTA GGAGCAGGTG 240

AATCTGGAAA AAGTACTATT GTTAAACAAA TGAAGATCAT CCACAAGAAT GGTTACAGTA 300

AACAAGAATG CATGGAGTTT AAAGCAGTGG TTTACAGTAA CACGTTGCAG TCCATCCTGG 360

CCATTGTGAA AGCCATGACT ACACTAGGGA TTGATTATGT CAATCCGAGA AGTAGAGAGG 420

ACCAACAACT GCTTCTCTCC ATGGCAAACA CACTAGAAGA TGGTGACATG ACGCCTCAGT 480

TGGCTGAAAT AATTAAACGT CTGTGGGGCG ATCCAGGAAT TCAAGCCTGC TTCGAAAGGG 540

CATCTGAATA CCAGCTCAAT GACTCTGCAG CTTACTACCT TAATGACTTA GATAGACTCA 600

CAGCCCCTGG GTATGTGCCA AATGAACAAG ACGTTCTACA TTCCCGGGTG AAAACCACTG 660

GTATCATTGA AACTCAATTC TCCTTTAAAG ACTTGAACTT CAGAATGTTT GATGTAGGTG 720

GCCAGAGATC AGAAAGAAAG AAATGGATCC ACTGCTTTGA AGGAGTGACG TGCATTATAT 780

TTTGTGCAGC CCTAAGTGCC TACGACATGG TACTTGTAGA AGATGAAGAG GTGAACAGAA 840

TGCATGAAAG TCTTCACCTC TTCAACAGCA TCTGTAATCA CAAGTATTTT GCAACCACCT 900

CCATTGTTCT GTTTCTTAAC AAGAAAGATC TCTTCCAGGA GAAAGTGACC AAGGTGCACC 960

TCAGCATCTG TTTCCCAGAA TACACTGGAC CAAATACATT CGAAGATGCA GGGAACTACA 1020

TCAAGAACCA GTTCCTAGAC CTGAACTTAA AAAAAGAAGA TAAGGAAATC TATTCTCACA 1080

TGACCTGCGC TACTGACACA CAAAACGTCA AATTCGTGTT TGATGCCGTG ACAGATATAA 1140

TAATAAAAGA GAACCTCAAA GACTGTGGGC TCTTCTGAGC AACCTGTTTG CTACCACTTG 1200

TGATGGCTAT AGTCTTTTTA AGACATAAAA AGGTGCTGTG TATTAGCTTG GATAGATATT 1260

AACTGATTTA GAAATGTGAC TAGCATTATA AAACAAAAAA ATTCACACAA AAATATTACT 1320

GTGATATCAC GTATATCTGG GTACGGTTTT CTTGGGGAAT GGAGGGTAGA GTTGCTGATG 1380

TTCTAAATCT GAAATCTGAT GTATCTGGTA ACTGTCACAA TATACATTCA TGCTACTAAA 1440

GTTTTTTGGA AGTGAGCTGT AAGTGACCAA TTTTTAATCA TAGAGTAAAC CTCAGAATGT 1500

-continued

GCTATAACAT TGCCCCAGCT AGATTTTGAA AGCATTCAAA GTCATGTCTG TACTACAGAA 1560

ACTGTACAAA ATGAACAAGG TATAATTTTG GTCATCAGCC TTTCAATTAG GCTGCCACAA 1620

GCACACACAG TACATGCTTT TATTGATGGG AAATTGTATG TGTAAAATAA ATATATATAT 1680

AATAAAAAAA AAAAAAAAAA AAA 1703

( 2 ) INFORMATION FOR SEQ ID NO:12:

( i ) SEQUENCE CHARACTERISTICS:
( A ) LENGTH: 354 amino acids
( B ) TYPE: amino acid
( D ) TOPOLOGY: linear ( i i ) MOLECULE TYPE: protein ( x i ) SEQUENCE DESCRIPTION: SEQ ID NO:12:

Met Gly Ser Gly Ile Ser Ser Glu Ser Lys Glu Ser Ala Lys Arg Ser
1 5 10 15

Lys Glu Leu Glu Lys Lys Leu Gln Glu Asp Ala Glu Arg Asp Ala Arg
20 25 30

Thr Val Lys Leu Leu Leu Leu Gly Ala Gly Glu Ser Gly Lys Ser Thr
35 40 45

Ile Val Lys Gln Met Lys Ile Ile His Lys Asn Gly Tyr Ser Lys Gln
50 55 60

Glu Cys Met Glu Phe Lys Ala Val Val Tyr Ser Asn Thr Leu Gln Ser
65 70 75 80

Ile Leu Ala Ile Val Lys Ala Met Thr Thr Leu Gly Ile Asp Tyr Val
85 90 95

Asn Pro Arg Ser Arg Glu Asp Gln Gln Leu Leu Leu Ser Met Ala Asn
100 105 110

Thr Leu Glu Asp Gly Asp Met Thr Pro Gln Leu Ala Glu Ile Ile Lys
115 120 125

Arg Leu Trp Gly Asp Pro Gly Ile Gln Ala Cys Phe Glu Arg Ala Ser
130 135 140

Glu Tyr Gln Leu Asn Asp Ser Ala Ala Tyr Tyr Leu Asn Asp Leu Asp
145 150 155 160

Arg Leu Thr Ala Pro Gly Tyr Val Pro Asn Glu Gln Asp Val Leu His
165 170 175

Ser Arg Val Lys Thr Thr Gly Ile Ile Glu Thr Gln Phe Ser Phe Lys
180 185 190

Asp Leu Asn Phe Arg Met Phe Asp Val Gly Gly Gln Arg Ser Glu Arg
195 200 205

Lys Lys Trp Ile His Cys Phe Glu Gly Val Thr Cys Ile Ile Phe Cys
210 215 220

Ala Ala Leu Ser Ala Tyr Asp Met Val Leu Val Glu Asp Glu Glu Val
225 230 235 240

Asn Arg Met His Glu Ser Leu His Leu Phe Asn Ser Ile Cys Asn His
245 250 255

Lys Tyr Phe Ala Thr Thr Ser Ile Val Leu Phe Leu Asn Lys Lys Asp
260 265 270

Leu Phe Gln Glu Lys Val Thr Lys Val His Leu Ser Ile Cys Phe Pro
275 280 285

Glu Tyr Thr Gly Pro Asn Thr Phe Glu Asp Ala Gly Asn Tyr Ile Lys
290 295 300

Asn Gln Phe Leu Asp Leu Asn Leu Lys Lys Glu Asp Lys Glu Ile Tyr
305 310 315 320

-continued

Ser His Met Thr Cys Ala Thr Asp Thr Gln Asn Val Lys Phe Val Phe
325 330 335

Asp Ala Val Thr Asp Ile Ile Ile Lys Glu Asn Leu Lys Asp Cys Gly
340 345 350

Leu Phe ( 2 ) INFORMATION FOR SEQ ID NO:13:

( i ) SEQUENCE CHARACTERISTICS:
( A ) LENGTH: 354 amino acids
( B ) TYPE: amino acid
( D ) TOPOLOGY: linear ( i i ) MOLECULE TYPE: protein ( x i ) SEQUENCE DESCRIPTION: SEQ ID NO:13:

Met Gly Ser Gly Ala Ser Ala Glu Asp Lys Glu Leu Ala Lys Arg Ser
1 5 10 15

Lys Glu Leu Glu Lys Lys Leu Gln Glu Asp Ala Asp Lys Glu Ala Lys
20 25 30

Thr Val Lys Leu Leu Leu Leu Gly Ala Gly Glu Ser Gly Lys Ser Thr
35 40 45

Ile Val Lys Gln Met Lys Ile Ile His Gln Asp Gly Tyr Ser Pro Glu
50 55 60

Glu Cys Leu Glu Tyr Lys Ala Ile Ile Tyr Gly Asn Val Leu Gln Ser
65 70 75 80

Ile Leu Ala Ile Ile Arg Ala Met Pro Thr Leu Gly Ile Asp Tyr Ala
85 90 95

Glu Val Ser Cys Val Asp Asn Gly Arg Gln Leu Asn Asn Leu Ala Asp
100 105 110

Ser Ile Glu Glu Gly Thr Met Pro Pro Glu Leu Val Glu Val Ile Arg
115 120 125

Lys Leu Trp Lys Asp Gly Gly Val Gln Ala Cys Phe Asp Arg Ala Ala
130 135 140

Glu Tyr Gln Leu Asn Asp Ser Ala Ser Tyr Tyr Leu Asn Gln Leu Asp
145 150 155 160

Arg Ile Thr Ala Pro Asp Tyr Leu Pro Asn Glu Gln Asp Val Leu Arg
165 170 175

Ser Arg Val Lys Thr Thr Gly Ile Ile Glu Thr Lys Phe Ser Val Lys
180 185 190

Asp Leu Asn Phe Arg Met Phe Asp Val Gly Gly Gln Arg Ser Glu Arg
195 200 205

Lys Lys Trp Ile His Cys Phe Glu Gly Val Thr Cys Ile Ile Phe Cys
210 215 220

Ala Ala Leu Ser Ala Tyr Asp Met Val Leu Val Glu Asp Asp Glu Val
225 230 235 240

Asn Arg Met His Glu Ser Leu His Leu Phe Asn Ser Ile Cys Asn His
245 250 255

Lys Phe Phe Ala Ala Thr Ser Ile Val Leu Phe Leu Asn Lys Lys Asp
260 265 270

Leu Phe Glu Glu Lys Ile Lys Lys Val His Leu Ser Ile Cys Phe Pro
275 280 285

Glu Tyr Asp Gly Asn Asn Ser Tyr Glu Asp Ala Gly Asn Tyr Ile Lys
290 295 300

Ser Gln Phe Leu Asp Leu Asn Met Arg Lys Asp Val Lys Glu Ile Tyr
305 310 315 320

-continued

Ser His Met Thr Cys Ala Thr Asp Thr Gln Asn Val Lys Phe Val Phe
325 330 335

Asp Ala Val Thr Asp Ile Ile Ile Lys Glu Asn Leu Lys Asp Cys Gly
340 345 350

Leu Phe (2) INFORMATION FOR SEQ ID NO:14:

(i) SEQUENCE CHARACTERISTICS:
(A) LENGTH: 350 amino acids
(B) TYPE: amino acid
(D) TOPOLOGY: linear (ii) MOLECULE TYPE: protein (xi) SEQUENCE DESCRIPTION: SEQ ID NO:14:

Met Gly Ala Gly Ala Ser Ala Glu Glu Lys His Ser Arg Glu Leu Glu
1 5 10 15

Lys Lys Leu Lys Glu Asp Ala Glu Lys Asp Ala Arg Thr Val Lys Leu
20 25 30

Leu Leu Leu Gly Ala Gly Glu Ser Gly Lys Ser Thr Ile Val Lys Gln
35 40 45

Met Lys Ile Ile His Gln Asp Gly Tyr Ser Leu Glu Glu Cys Leu Glu
50 55 60

Phe Ile Ala Ile Ile Tyr Gly Asn Thr Leu Gln Ser Ile Leu Ala Ile
65 70 75 80

Val Arg Ala Met Thr Thr Leu Asn Ile Gln Tyr Gly Asp Ser Ala Arg
85 90 95

Gln Asp Asp Ala Arg Lys Leu Met His Met Ala Asp Thr Ile Glu Glu
100 105 110

Gly Thr Met Pro Lys Glu Met Ser Asp Ile Ile Gln Arg Leu Trp Lys
115 120 125

Asp Ser Gly Ile Gln Ala Cys Phe Asp Arg Ala Ser Glu Tyr Gln Leu
130 135 140

Asn Asp Ser Ala Gly Tyr Tyr Leu Ser Asp Leu Glu Arg Leu Val Thr
145 150 155 160

Pro Gly Tyr Val Pro Thr Glu Gln Asp Val Leu Arg Ser Arg Val Lys
165 170 175

Thr Thr Gly Ile Ile Glu Thr Gln Phe Ser Phe Lys Asp Leu Asn Phe
180 185 190

Arg Met Phe Asp Val Gly Gly Gln Arg Ser Glu Arg Lys Lys Trp Ile
195 200 205

His Cys Phe Glu Gly Val Thr Cys Ile Ile Phe Ile Ala Ala Leu Ser
210 215 220

Ala Tyr Asp Met Val Leu Val Glu Asp Asp Glu Val Asn Arg Met His
225 230 235 240

Glu Ser Leu His Leu Phe Asn Ser Ile Cys Asn His Arg Tyr Phe Ala
245 250 255

Thr Thr Ser Ile Val Leu Phe Leu Asn Lys Lys Asp Val Phe Ser Glu
260 265 270

Lys Ile Lys Lys Ala His Leu Ser Ile Cys Phe Pro Asp Tyr Asn Gly
275 280 285

Pro Asn Thr Tyr Glu Asp Ala Gly Asn Tyr Ile Lys Val Gln Phe Leu
290 295 300

Glu Leu Asn Met Arg Arg Asp Val Lys Glu Ile Tyr Ser His Met Thr
305 310 315 320

Cys Ala Thr Asp Thr Gln Asn Val Lys Phe Val Phe Asp Ala Val Thr
325 330 335

Asp Ile Ile Ile Lys Glu Asn Leu Lys Asp Cys Gly Leu Phe
340 345 350

( 2 ) INFORMATION FOR SEQ ID NO:15:

( i ) SEQUENCE CHARACTERISTICS:
( A ) LENGTH: 354 amino acids
( B ) TYPE: amino acid
( D ) TOPOLOGY: linear ( i i ) MOLECULE TYPE: protein ( i x ) FEATURE:
( D ) OTHER INFORMATION: /note="Positions indicated as Xaa represent nonconserved amino acids."

( x i ) SEQUENCE DESCRIPTION: SEQ ID NO:15:

Met Gly Ser Gly Ala Ser Ala Glu Xaa Lys Glu Xaa Ala Lys Arg Ser
1 5 10 15

Lys Glu Leu Glu Lys Lys Leu Gln Glu Asp Ala Glu Lys Asp Ala Arg
20 25 30

Thr Val Lys Leu Leu Leu Leu Gly Ala Gly Glu Ser Gly Lys Ser Thr
35 40 45

Ile Val Lys Gln Met Lys Ile Ile His Gln Asp Gly Tyr Ser Xaa Glu
50 55 60

Glu Cys Leu Glu Phe Lys Ala Ile Ile Tyr Gly Asn Thr Leu Gln Ser
65 70 75 80

Ile Leu Ala Ile Val Arg Ala Met Thr Thr Leu Gly Ile Asp Tyr Xaa
85 90 95

Xaa Xaa Xaa Xaa Xaa Asp Asp Xaa Arg Xaa Leu Xaa Xaa Met Ala Asp
100 105 110

Thr Ile Glu Glu Gly Thr Met Pro Pro Glu Leu Xaa Glu Ile Ile Xaa
115 120 125

Arg Leu Trp Lys Asp Xaa Gly Ile Gln Ala Cys Phe Asp Arg Ala Ser
130 135 140

Glu Tyr Gln Leu Asn Asp Ser Ala Xaa Tyr Tyr Leu Asn Asp Leu Asp
145 150 155 160

Arg Leu Thr Ala Pro Gly Tyr Val Pro Asn Glu Gln Asp Val Leu Arg
165 170 175

Ser Arg Val Lys Thr Thr Gly Ile Ile Glu Thr Gln Phe Ser Phe Lys
180 185 190

Asp Leu Asn Phe Arg Met Phe Asp Val Gly Gly Gln Arg Ser Glu Arg
195 200 205

Lys Lys Trp Ile His Cys Phe Glu Gly Val Thr Cys Ile Ile Phe Cys
210 215 220

Ala Ala Leu Ser Ala Tyr Asp Met Val Leu Val Glu Asp Asp Glu Val
225 230 235 240

Asn Arg Met His Glu Ser Leu His Leu Phe Asn Ser Ile Cys Asn His
245 250 255

Lys Tyr Phe Ala Thr Thr Ser Ile Val Leu Phe Leu Asn Lys Lys Asp
260 265 270

Leu Phe Xaa Glu Lys Ile Lys Lys Val His Leu Ser Ile Cys Phe Pro
275 280 285

Glu Tyr Xaa Gly Pro Asn Thr Tyr Glu Asp Ala Gly Asn Tyr Ile Lys
290 295 300

Xaa Gln Phe Leu Asp Leu Asn Met Arg Lys Asp Val Lys Glu Ile Tyr

```
305                      310                      315                      320

Ser His Met Thr Cys Ala Thr Asp Thr Gln Asn Val Lys Phe Val Phe
                325                      330                      335

Asp Ala Val Thr Asp Ile Ile Ile Lys Glu Asn Leu Lys Asp Cys Gly
            340                      345                      350

Leu Phe
```

( 2 ) INFORMATION FOR SEQ ID NO:16:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:16:

```
Lys Trp Ile His Cys Phe
1               5
```

( 2 ) INFORMATION FOR SEQ ID NO:17:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:17:

```
CGGATCCAAR TGGATHCAYT GYTT                                  24
```

( 2 ) INFORMATION FOR SEQ ID NO:18:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:18:

```
Phe Leu Asn Lys Lys Asp
1               5
```

( 2 ) INFORMATION FOR SEQ ID NO:19:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:19:

```
GGAATTCRTC YTTYTTRTTN AGRAA                                 25
```

( 2 ) INFORMATION FOR SEQ ID NO:20:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:20:

GGAATTCRTC YTTYTTRTTY AARAA 25

( 2 ) INFORMATION FOR SEQ ID NO:21:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:21:

Asp Val Gly Gly Gln Arg
1 5

( 2 ) INFORMATION FOR SEQ ID NO:22:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:22:

GTCTAGAGAY GTNGGNGGNC ARMG 24

( 2 ) INFORMATION FOR SEQ ID NO:23:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:23:

Val Phe Asp Ala Val Thr Asp
1 5

( 2 ) INFORMATION FOR SEQ ID NO:24:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:24:

CCGAATTCTC NGTNACNGCR TCRAANAC 28

( 2 ) INFORMATION FOR SEQ ID NO:25:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:25:

Thr Ile Val Lys Gln Met
1 5

( 2 ) INFORMATION FOR SEQ ID NO:26:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

CCGAATTCAC NATNGTNAAR CARATG 26

( 2 ) INFORMATION FOR SEQ ID NO:27:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:27:

Phe Leu Asn Lys Gln Asp
1 5

( 2 ) INFORMATION FOR SEQ ID NO:28:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:28:

CCGAATTCRT CYTGYTTRTT NARRAA 26

( 2 ) INFORMATION FOR SEQ ID NO:29:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:29:

His Leu Phe Asn Ser Ile Cys
1 5

( 2 ) INFORMATION FOR SEQ ID NO:30:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:30:

CCGGATCCGC ACCTGTTCAA CAGCATCT 28

( 2 ) INFORMATION FOR SEQ ID NO:31:

( i ) SEQUENCE CHARACTERISTICS:
( A ) LENGTH: 7 amino acids ( B ) TYPE: amino acid
( D ) TOPOLOGY: linear ( i i ) MOLECULE TYPE: peptide ( x i ) SEQUENCE DESCRIPTION: SEQ ID NO:31:

Lys Tyr Phe Ala Thr Thr Ser
1 5

( 2 ) INFORMATION FOR SEQ ID NO:32:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:32:

CCGGATCCGA GGTGGTTGCA AAATACTT 28

( 2 ) INFORMATION FOR SEQ ID NO:33:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Leu Ala Glu Ile Ile Lys Arg
1 5

( 2 ) INFORMATION FOR SEQ ID NO:34:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:34:

CGGATCCGAC GTTTAATTAT TTCAGCCAA 29

( 2 ) INFORMATION FOR SEQ ID NO:35:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:35:

TCGACCCACG CGTCCG 16

( 2 ) INFORMATION FOR SEQ ID NO:36:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear -continued ( i i ) MOLECULE TYPE: DNA ( x i ) SEQUENCE DESCRIPTION: SEQ ID NO:36:

GGGCGGCCGC 10